United States Patent [19]

Santilli et al.

[11] 4,452,985
[45] Jun. 5, 1984

[54] 2-GUANYL-4-(SUBSTITUTED PHENYL) THIAZOLE DERIVATIVES

[75] Inventors: Arthur A. Santilli, Havertown; Anthony C. Scotese, King of Prussia; Robert L. Morris, Devon; Stanley C. Bell, Penn Valley, all of Pa.

[73] Assignee: American Home Products Corporation, New York, N.Y.

[21] Appl. No.: 466,239

[22] Filed: Feb. 14, 1983

[51] Int. Cl.³ ................. C07D 277/46; A61K 31/425
[52] U.S. Cl. .................................... 548/131; 548/193; 548/194; 548/197; 548/198; 424/269; 424/270
[58] Field of Search ............... 548/131, 190, 194, 196, 548/197, 198

[56] References Cited
FOREIGN PATENT DOCUMENTS
060093 9/1982 European Pat. Off. ............ 548/198

Primary Examiner—Robert Gerstl
Attorney, Agent, or Firm—George Tarnowski

[57] ABSTRACT

Compounds of the formula:

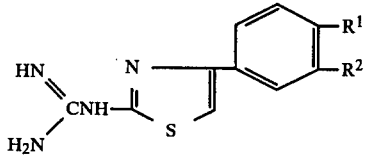

wherein
R¹ is hydrogen, cyano or cyano(lower)alkyl;
R² is hydrogen, cyano, carboxy, carbamoyl, guanyl, (lower)alkoxyimino, hydrazinocarbonyl, (lower)alkylaminoimino,

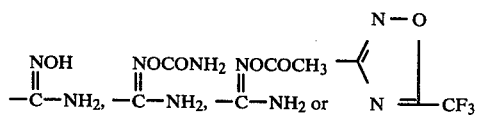

with the proviso that one but never both of R¹ and R² is hydrogen; and the pharmacologically acceptable salts thereof exhibit H₂-receptor antagonist and gastric secretion inhibition activity.

9 Claims, No Drawings

2-GUANYL-4-(SUBSTITUTED PHENYL) THIAZOLE DERIVATIVES

This invention relates to new 2-guanyl-4-(substituted phenyl)thiazole compounds having a selective action on $H_2$ histamine receptors and which inhibit gastric acid secretion.

It has been postulated that the physiologically active compound histamine, which occurs naturally within the animal body, is able to combine, in the course of exerting its activity, with certain specific receptors of which there are at least two distinct and separate types. The first has been named the $H_1$ receptor (Ash and Schild, Brit. J. Pharmac., 1966, 27, 427) and the action of histamine at this receptor is blocked (antagonized) by classical "antihistamine" drugs such as mepyramine (pyrilamine). The second histamine receptor has been named the $H_2$ receptor (Black et al., Nature, 1972, 236, 385) and the action of histamine at this receptor is blocked by drugs such as cimetidine. It is known that one of the results of the blockage of the action of histamine at the $H_2$ receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

The commercialization of cimetidine and subsequent follow-up pharmacological research in patients has demonstrated that cimetidine is a drug with limitations, such as short duration of action, anti-androgenic activity, and a tendency to cause confusional states in elderly patients. Obviously, much intensive research has been carried out to find improved $H_2$ antagonists. Indeed, selective $H_2$ antagonists having greater activity than cimetidine have been discovered. Among the better known new $H_2$ antagonists are ranitidine (disclosed in U.S. Pat. No. 4,128,658) having the structure:

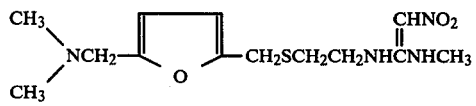

tiotidine (U.S. Pat. No. 4,165,378) having the structure:

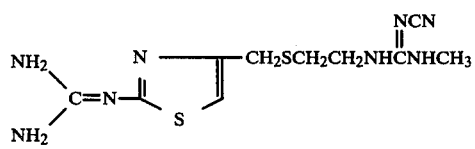

and compounds such as those disclosed in European patent application No. 3,640 having the structure:

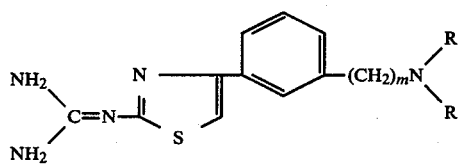

There has now been discovered a novel group of compounds with $H_2$ receptor antagonist and gastric secretion inhibition activity, having the following formula:

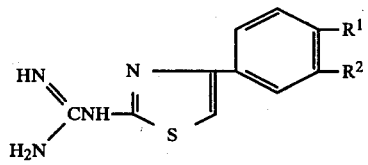

wherein
  $R^1$ is hydrogen, cyano or cyano(lower)alkyl;
  $R^2$ is hydrogen, cyano, carboxy, carbamoyl, guanyl, (lower)alkoxyimino, hydrazinocarbonyl, (lower)alkylaminoimino,

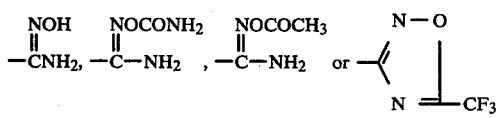

with the proviso that one but never both of $R^1$ and $R^2$ is hydrogen, and the pharmacologically acceptable salts thereof.

The terms "lower alkyl" and "lower alkoxy" refer to moieties having 1-6 carbon atoms in the carbon chain.

The compounds of the invention can be readily prepared by reacting a suitably m- or p-substituted α-bromoacetophenone with amidinothiourea in an organic solvent according to the following reaction sequence:

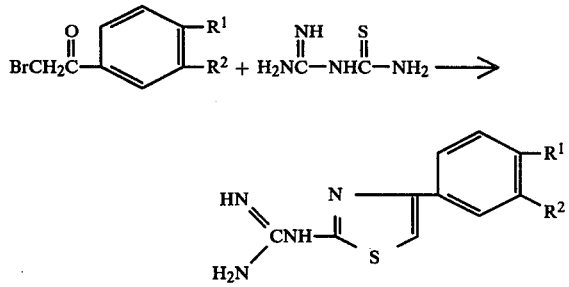

The compounds in which $R^1$ is cyano or cyano(lower)alkyl and $R^2$ is hydrogen, and those in which $R^2$ is cyano and $R^1$ is hydrogen are prepared directly by the above outlined method. In those instances in which $R^2$ is carboxy or

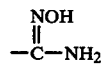

and $R^1$ is hydrogen, can be prepared by reacting [4-(3-cyanophenyl)-2-thiazolyl]guanidine with an acid or hydroxylamine:

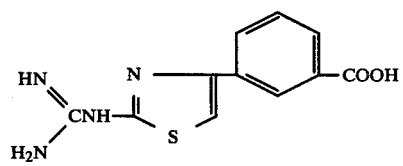

-continued

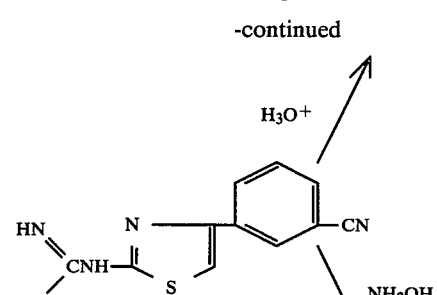

Those compounds in which R² is

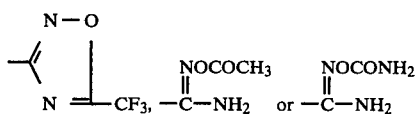

and R¹ is hydrogen are prepared by further reacting 3-[2-[(aminoiminomethyl)amino]-4-thiazolyl]-N-hydroxylbenzenecarboximidamide with trifluoroacetic anhydride, acetic anhydride or potassium cyanate, respectively:

Those compounds in which R² is (lower)alkylimino, (lower)alkylaminoimino or carbamoyl can be prepared by reacting 3-(bromoacetyl)benzenecarboximidic acid lower alkyl ester and 3-(bromoacetyl)benzenecarboxamide with amidinothiourea according to the following reaction sequence (where R represents lower alkyl):

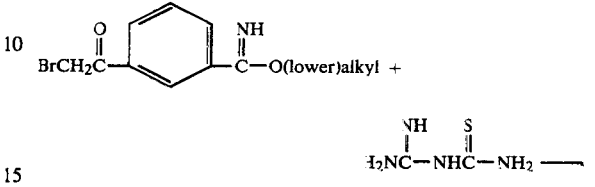

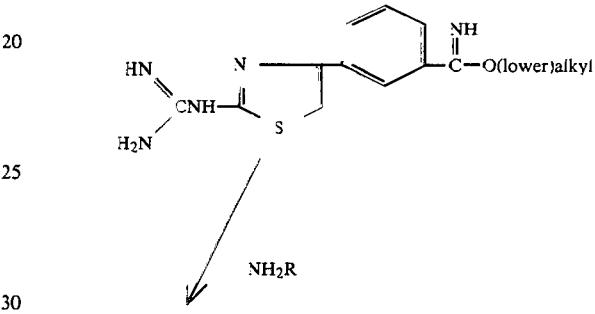

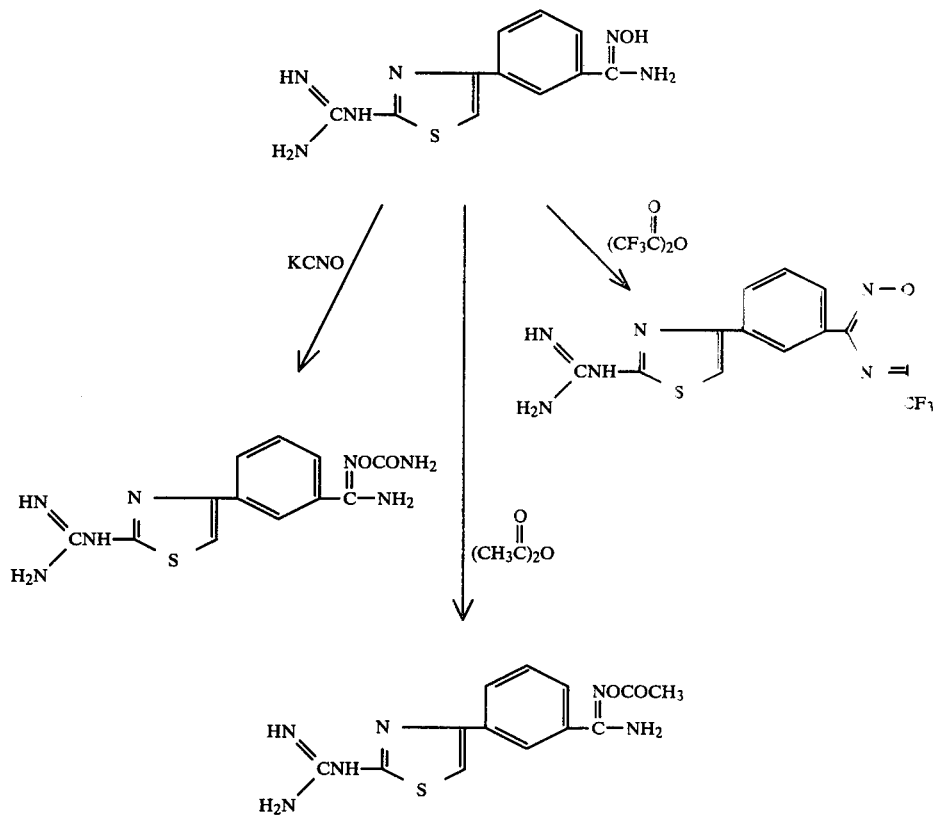

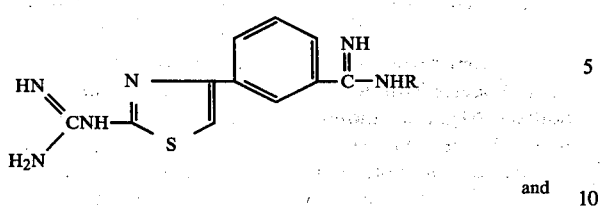

and

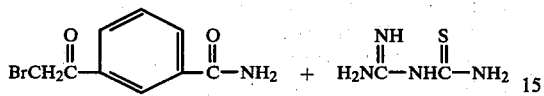

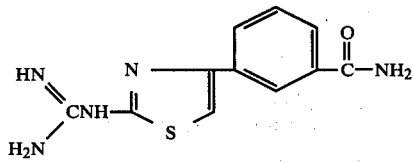

The starting compounds in the above sequence, 3-(bromoacetyl)benzenecarboximidic acid lower alkyl ester and 3-(bromoacetyl)benzenecarboxamide are prepared by the following reaction sequence from m-cyanoacetophenone:

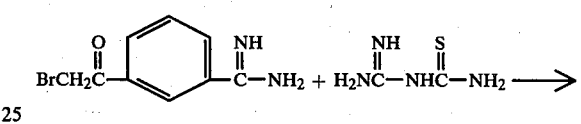

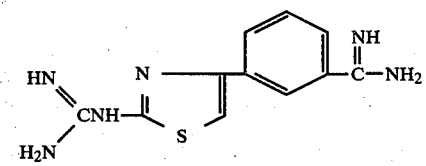

When it is desired to obtain the compound in which $R^2$ is guanyl and $R^1$ is hydrogen, the immediately preceding intermediate preparation sequence is modified as follows:

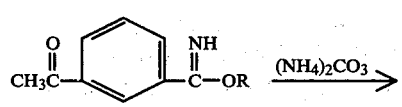

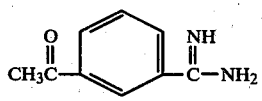

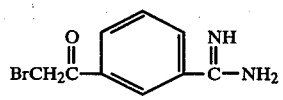

This intermediate is then reacted with amidinothiourea as usual to obtain the desired final product:

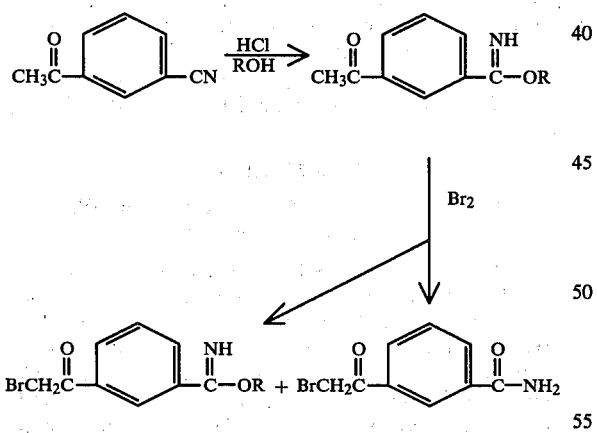

Finally, the compound in which $R^2$ is hydrazinocarbonyl and $R^1$ is hydrogen can be prepared according to the following reaction sequence, in which the starting compound is 3-bromoacetylbenzoic acid (lower)alkyl ester (where R represents (lower)alkyl):

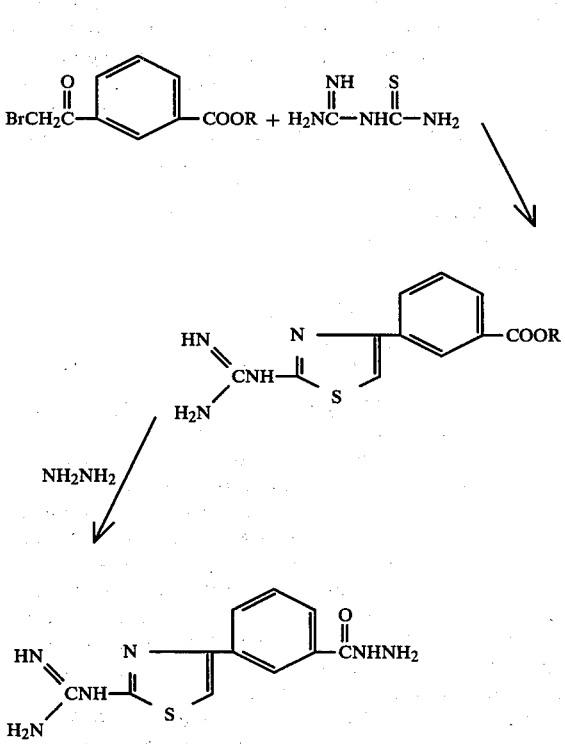

In all cases, the starting compound substituted-benzophenones are available commercially or can be prepared by conventional means.

The compounds of the invention readily form pharmacologically acceptable salts with both inorganic and organic acids, such as hydrochloric, hydrobromic, sulfuric, nitric, phosphoric, acetic, maleic, fumaric, citric and the like.

The compounds of the invention exhibit potent histamine $H_2$-blocking activity and gastric secretion inhibition activity, and can be used in the treatment of conditions where there is hypersecretion of gastric acid, such as in gastric and peptic ulceration, and other conditions caused or exacerbated by gastric acidity such as stress ulceration or gastric intestinal bleeding due to trauma.

The compounds of the invention can be administered orally or parenterally or by suppository, of which the preferred route is the oral route. They may be used in the form of the base or as a pharmacologically acceptable salt. They will in general be associated with a pharmaceutically acceptable carrier or diluent, to provide a pharmaceutical composition.

The compounds of the invention can be administered in combination with other active ingredients, e.g. conventional antihistamines, if required. For oral administration the pharmaceutical composition can most conveniently be in the form of capsules or tablets, which may be slow release tablets. The composition may also take the form of a dragee or may be in syrup form.

A convenient daily dose by the oral route would be of the order of 100 mg. to 1.2 g. per day, in the form of dosage units containing from 20 to 200 mg. per dosage unit. A convenient regimen in the case of a slow release tablet would be twice or three times a day.

Parenteral administration may be by injections at intervals or as a continuous infusion. Injection solutions may contain from 10 to 100 mg/ml. of active ingredient.

The histamine $H_2$-antagonist activity of the compounds of the invention may be demonstrated by the ability of the compounds to inhibit the histamine-induced positive chronotropic response in the spontaneously beating right atrium of the guinea pig heart, as well as by activity in other more generalized procedures, such as the modified Shay procedure of pylorus ligation for the study of rat gastric secretion.

The procedures for these tests and the results for some of the compounds of the invention are presented at the end of the following examples, which will serve to illustrate the present invention.

EXAMPLE 1

[4-(4-Cyanophenyl)-2-Thiazolyl]Guanidine, Hydrobromide

To a solution of 14.5 g. (0.1 mole) of p-acetylbenzonitrile in 250 ml. of methylene chloride is added 16.0 g. (0.1 mole) of bromine. After a few minutes of stirring at room temperature, the solution turns colorless. Stirring is continued an additional 15 minutes. The methylene chloride is removed on a rotary evaporator and 350 ml. of ethanol is added to the residue. To the suspension is added 11.8 g. (0.1 mole) of amidinothiourea. The reaction mixture is heated under reflux for 1 hour, then cooled in ice. The precipitate which forms amounts to 26.9 g. Recrystallization from DMF-EtOH gives 22.4 g. of product with m.p. 293°–295°.

Analysis for: $C_{11}H_{10}BrN_5S$: Calculated: C, 40.75; H, 3.11; N, 21.60; Found: C, 40.63; H, 3.17; N, 21.79.

EXAMPLE 2

[4-[4-(Cyanomethyl)Phenyl]-2-Thiazolyl]Guanidine, Hydrobromide

To a stirred solution of 6.36 g. (0.04 mole) of p-acetylphenyl acetonitrile in 100 ml. of methylene chloride is added 6.40 g. (0.04 mole) of bromine in 50 ml. of methylene chloride. The reaction solution is warmed for a few minutes and the heat then removed. After a few minutes the bromine color disappears. The reaction mixture is stirred an additional ½ hour at room temperature. The methylene chloride is removed in vacuo on a rotary evaporator. To the residue is added 100 ml. of ethanol and 4.73 g. (0.04 mole) of amidinothiourea. The reaction mixture is heated with stirring for 1 hour under reflux, cooled in ice and then filtered. There is obtained 7.6 g. of product, m.p. 242°–246° (dec.). Recrystallization is from ethanol to which is then added enough water to form a solution. Ether is added to the cloudy point. There is obtained 5.9 g. of crystals, m.p. 259°–261° (dec.).

Analysis for: $C_{12}H_{11}N_5S \cdot HBr$: Calculated: C, 42.61; H, 3.58; N, 20.71; Found: C, 42.25; H, 3.73; N, 20.55.

EXAMPLE 3

[4-(3-Cyanophenyl)-2-Thiazolyl]Guanidine, Hydrobromide, Hydrate

To a solution of 4.35 g. (0.03 mole) of m-cyanoacetophenone in 75 ml. of chloroform is addded 4.77 g. (0.03 mole) of bromine. The solution is stirred at room temperature for 20 minutes. The solution is then evaporated in a rotary evaporator and the residue is dissolved in 20 ml. of acetonitrile. To this solution is added a hot solution of 3.54 g. (0.03 mole) of amidinothiourea in 75 ml. of ethanol. The mixture is heated under reflux for 1 hour. The mixture is filtered and the filter cake is recrystallized from water. The material is dried in an oven at 100° C. under vacuum and is then left uncovered at room temperature for three hours to provide 2.4 g. of product, m.p. 292°–294° (dec.).

Analysis for: $C_{11}H_{10}N_5BrS \cdot H_2O$: Calculated: C, 38.60; H, 3.54; N, 20.47; Found C, 38.65; H, 3.35; N, 20.49.

EXAMPLE 4

3-[2-[(Aminoiminomethyl)Amino]-4-Thiazolyl]Benzoic Acid, Hydrochloride

A mixture of 1 g. of [4-(3-cyanophenyl)-2-thiazolyl]-guanidine of Example 3 is heated under reflux in 30 ml. of concentrated hydrochloric acid for 12 hours. The mixture is filtered and the filter cake is triturated with 50 ml. of 20% aqueous sodium hydroxide. The insoluble material is filtered off and the filtrate is acidified with concentrated hydrochloric acid. The precipitate which forms is collected and is recrystallized from ethanol (water is added to provide a solution) to give 0.3 g. of product, m.p. 305°–307° (dec.).

Analysis for: $C_{11}H_{10}N_3O_2S \cdot HCl$: Calculated: C, 44.22; H, 3.71; N, 18.75; Found: C, 44.05; H, 3.82; N, 18.84.

EXAMPLE 5

3-[2-[(Aminoiminomethyl)Amino]-4-Thiazolyl]-N-Hydroxybenzenecarboximidamide, Dihydrochloride A stirred mixture of 3.4 g. (0.01 mole) of [4-(3-cyanophenyl)-2-thiazolyl]guanidine of Example 3, 1.38 g.

(0.02 mole) of hydroxylamine hydrochloride and 4.24 g. (0.04 mole) of sodium carbonate in 60 ml. of dry N,N-dimethylformamide is heated under reflux for 6 hours. The mixture is filtered and the filtrate is diluted with a little water. The precipitate which forms is collected and is recrystallized from N,N-dimethylformamide. This solid is added to 150 ml. of a saturated ethanolic hydrochloric acid solution and the mixture is quickly filtered. The filtrate is cooled in ice to precipitate 0.4 g. of product, m.p. 246° (dec.).

Analysis for: $C_{11}H_{12}N_6OS.2HCl$: Calculated: C, 37.83; H, 4.04; N, 24.07; Found: C, 37.68; H, 4.02; N, 23.80.

EXAMPLE 6

N-[(Aminocarbonyl)oxy]-3-[2-[(Aminoiminomethyl)Amino]-4-Thiazolyl]Benzenecarboximidamide, Hydrochloride, Hemihydrate To a solution of 0.698 g. (0.002 mole) of 3-[2-[aminoiminomethyl)amino]-4-thiazolyl]-N-hydroxybenzenecarboximidamide, dihydrochloride of Example 5 in 40 ml. of water is added 0.162 g. (0.002 mole) of potassium cyanate. The mixture is stirred at room temperature for 2 hours. The insoluble material is collected and is dissolved in boiling water. The water solution is diluted with ethanol to twice its volume and is cooled in ice. The precipitate which forms is collected to give 0.3 g. of product, m.p. 222°-224° (dec.).

Analysis for: $C_{12}H_{14}ClN_7O_2S.\frac{1}{2}H_2O$: Calculated: C, 39.51; H, 4.14; N, 26.89; Found: C, 39.26; H, 4.03; N, 26.91.

EXAMPLE 7

N-(Acetyloxy)-3-[[2-[(Aminoiminomethyl)Amino]-4-Thiazolyl]Benzenecarboximidamide, Dihydrochloride A mixture of 1 g. of finely ground 3-[2-[(aminoiminomethyl)amino]-4-thiazolyl]-N-hydroxybenzenecarboximidamide of Example 5 in 150 ml. of acetic anhydride is stirred at room temperature for 1 hour. The mixture is filtered and the filter cake is triturated with 100 ml. of 20% aqueous sodium carbonate solution. The insoluble material is collected, air dried and is recrystallized from 2-ethoxyethanol (ethanol and petroleum ether are added to initiate precipitation). The purified free base is added to 50 ml. of a hot saturated ethanolic hydrochloric acid solution. The solution is cooled and is diluted with petroleum ether to the cloudy point. The precipitate which forms is collected to give 0.15 g. of product, m.p. 260° (dec.).

Analysis for: $C_{13}H_{14}N_6O_2S.2HCl$: Calculated: C, 39.90; H, 4.12; N, 21.48; Found: C, 40.25; H, 4.08; N, 21.61.

EXAMPLE 8

[4-[3-[5-(Trifluoromethyl)-1,2,4-Oxadiazol-3-yl]Phenyl]-2-Thiazoyl]Guanidine, Hydrochloride A mixture of 1 g. of 3-[2-[(aminoiminomethyl)amino]-4-thiazolyl]-N-hydroxybenzenecarboximidamide of Example 5 in 60 ml. of trifluoroacetic anhydride is stirred at room temperature for 30 minutes. The insoluble material is collected and the filter cake is treated with 50 ml. of a 20% aqueous sodium carbonate solution. The insoluble material is collected and is air dried. The material is recrystallized from ethanol. This purified free base is dissolved in hot ethanol and this solution is acidified with an ethereal hydrochloric acid solution. On cooling, the precipitate which forms is collected to give 0.4 g. of product, m.p. 240°-243°.

Analysis for: $C_{13}H_9N_6OSF_3.HCl$: Calculated: C, 39.95; H, 2.58; N, 21.51; Found: C, 39.85; H, 2.63; N, 21.39.

EXAMPLE 9

3-[2-[(Aminoiminomethyl)Amino]-4-Thiazolyl]Benzenecarboximidamide, Dihydrobromide, Hemiethanolate A. 3-Acetylbenzenecarboximidic Acid Ethyl Ester, Hydrochloride To an ice-water cooled solution of 29 g. (0.2 mole) of m-cyanoacetophenone in 375 ml. of dry toluene, containing 13 ml. (0.2 mole) of absolute ethanol, is bubbled a stream of hydrogen chloride gas for 2 hours. The solution is allowed to stand in a cold room overnight. The precipitate which forms is collected to give 34 g. of product. A small amount is recrystallized from ethanol (petroleum ether is added to initiate precipitation) to afford a sample with a melting point of 130°-132°.

B. 3-Acetylbenzenecarboximidamide, Hydrochloride

A mixture of 14 g. (0.08 mole) of 3-acetylbenzenecarboximidic acid ethyl ester, hydrochloride of A. above and 14 g. (0.15 mole) of finely ground ammonium carbonate in 100 ml. of ethanol is heated at boiling temperature in an open flask for 3 hours. The solution is cooled and the first small amount of precipitate is collected and is discarded. The filtrate is further cooled to precipitate 6.7 g. of product with a melting point of 193° (dec.).

C. 3-[2-(Aminoiminomethyl)Amino]-4-Thiazolyl]Benzenecarboximidamide, Dihydrobromide, Hemiethanolate A mixture of 3.96 g. (0.02 mole) of 3-acetylbenzenecarboximidamide of B. above in 25 ml. of glacial acetic acid is warmed to give a solution. The solution is cooled to room temperature and 3.18 g. (0.02 mole) of bromine is added. After stirring at room temperature for 15 minutes, the orange mixture is warmed to provide a solution. This solution is stirred for 20 minutes without further heat. The clear yellow solution is evaporated in a rotary evaporator using a hot water bath. The residual oil is dissolved in 50 ml. of a 50—50 mixture of acetonitrile-ethanol. To this solution is added 2.36 g. (0.2 mole) of amidinothiourea and the mixture is heated under reflux for 10 minutes and is filtered. The filter cake is recrystallized from boiling ethanol using a minimum amount of water to produce a solution. On cooling in ice, a precipitate is formed which is collected to give 3.0 g. of product, m.p. 315° (dec.).

Analysis for: $C_{11}H_{14}Br_2N_6S.\frac{1}{2}CH_3CH_2OH$: Calculated: C, 32.37; H, 3.85; N, 18.89; Found: C, 32.26; H, 3.74; N, 19.18.

EXAMPLE 10

3-[2-[(Aminoiminomethyl)Amino]-4-Thiazolyl]Benzenecarboximidic Acid Ethyl Ester

A. 3-(Bromoacetyl)Benzenecarboximidic Acid Ethyl Ester, Hydrobromide

To 350 ml. of glacial acetic warmed to 60° C. is added 4.54 g. (0.02 mole) of 3-acetylbenzenecarboximidic acid ethyl ester prepared as in Example 9A. To this solution is added 3.18 g. (0.02 mole) of bromine in one portion. The heat is removed and the solution is allowed to stir until the solution becomes almost colorless (about 1 hour). Anhydrous ethyl ether is added to the cloudy point. The precipitate which forms is collected to give 4.5 g. of a mixture (125° d.) of mostly 3-(bromoacetyl)-benzenecarboximidic acid ethyl ester, hydrobromide and a small amount of 3-(bromoacetyl)benzenecarboxamide. Recrystallization of this mixture from a large volume of ethyl acetate gives a sample with a very small amount of impurity, m.p. 130°-132°.

Analysis for: $C_{11}H_{13}Br_2NO_2$: Calculated: C, 37.63; H, 3.73; N, 3.99; Found: C, 37.21; H, 3.55; N, 3.87.

B. 3-[2-[(Aminoiminomethyl)Amino]-4-Thiazolyl]Benzenecarboximidic Acid Ethyl Ester A mixture of 3.5 g. (0.01 mole) of 3-(bromoacetyl)-benzenecarboximidic acid ethyl ester (about 90% pure) and 1.18 g. (0.01 mole) of amidinothiourea in 50 l. of ethanol is heated under reflux for 10 minutes. The mixture is filtered and the filter cake is dissolved in 75 ml. of water. The solution is made basic with a 20% sodium carbonate solution. The insoluble material is collected and is dissolved in 50 ml. of ethanol. The ethanol solution is diluted with 50 ml. of water and is cooled in ice. The precipitate which forms is collected. Recrystallization from ethanol gives 0.3 g. of product, m.p. 205°-207° (dec.).

Analysis for: $C_{13}H_{15}N_5OS$: Calculated: C, 53.96; H, 5.23; N, 24.20; Found: C, 53.75; H, 5.26; N, 24.07.

EXAMPLE 11

3-[2-[(Aminoiminomethyl)Amino]-4-Thiazolyl]Benzenecarboxamide, Hydrobromide

A. 3-(Bromoacetyl)Benzenecarboxamide

The filtrate from the recrystallization of 3-(bromoacetyl)benzenecarboximidic acid ethyl ester, hydrobromide from Example 10A. Above is evaporated to dryness. The residue is recrystallized from acetonitrile to give a first crop of solid. Further cooling of the filtrate produces a second crop of material. This second crop is recrystallized from ethyl acetate to give a mixture containing predominantly the desired amide, m.p. 133°-136°. The mixture is used in the next step without further purification.

B. 3-[2-[(Aminoiminomethyl)Amino]-4-Thiazolyl]Benzenecarboxamide, Hydrobromide

A stirred mixture of 0.48 (0.002 mole) of 3-(bromoacetyl)benzenecarboxamide (about 85% pure) and 0.236 g. (0.002 mole) of amidinothiourea in 20 ml. of a 50—50 mixture of acetonitrileethanol is heated under reflux for 5 minutes. The insoluble material is collected and is dissolved in the minimum amount of boiling water. The solution is diluted with ethanol to twice its volume and is cooled in ice. The precipitate which forms is collected to give 0.25 g. of product, m.p. 304°-306° (dec.).

Analysis for: $C_{11}H_{12}BrN_5OS$: Calculated: C, 38.60; H, 3.54; N, 20.46; Found: C, 38.54; H, 3.56; N, 20.33.

EXAMPLE 12

3-[2-[(Aminoiminomethyl)Amino]-4-Thiazolyl]-N-Methylbenzenecarboximidamide, Quarter Hydrate A mixture of 0.8 g. of 3-[2-[(aminoiminomethyl)amino]-4-thiazolyl]benzenecarboximidic acid ethyl ester, prepared as in Example 10, in 20 ml. of a saturated ethanolic methylamine solution is heated under reflux for 3 hours. The solution is cooled and is diluted with water to the cloudy point. The precipitate which forms is air dried and is recrystallized from acetonitrile twice to give 0.2 g. of product, m.p. 197°-199° (dec.).

Analysis for: $C_{12}H_{14}N_6S \cdot \frac{1}{4}H_2O$: Calculated: C, 51.68; H, 5.24; N, 30.14; Found: C, 51.96; H, 5.34; N, 30.13.

EXAMPLE 13

3-[2-[(Aminoiminomethyl)Amino]-4-Thiazolyl]Benzoic Acid Hydrazide, Hydrochloride To 10 ml. of 95% hydrazine is added 3-[2-[(aminoiminomethyl)amino]-4-thiazolyl]benzoic acid methyl ester (1.1 g., 0.004 mole). This is stirred for 1 hour at room temperature. The product precipitates out and is filtered off and rinsed with ethanol. The filtrate is reduced to dryness and ethanol is added to the residue, and the insoluble material is filtered off and combined with previously filtered solid to give a crude yield of about 1 g. of the carboxhydrazide. This crude solid is added to 40 ml. ethanol and to this is added 10 ml. of ethanolic HCl solution and the mixture is heated briefly at reflux temperature. The suspension that forms is filtered off and recrystallized from 90% aqueous ethanol to give 0.65 g. of the desired product, m.p. 275° C. (dec.).

Analysis for: $C_{11}H_{13}ClN_6OS$: Calculated: C, 42.24; H, 4.19; N, 26.87; Cl, 11.34; Found: C, 41.86; H, 4.27; N, 26.49; Cl, 11.11.

EXAMPLE 14

The guinea pig heart atrium test is carried out as follows:

A guinea pig right atrium is suspended at 1 g. tension (isometric) in a thermostatically controlled (32° C.) tissue bath (10 ml.) containing oxygenated (95% $O_2$; 5% $CO_2$) Krebs-Haenseleit buffer (pH 7.4). The tissue is allowed to stabilize over 1 hour. Individual contractions are recorded with a force-displacement transducer through a strain gauge coupler. A control dose-response curve to histamine in the above described tissue bath is obtained after which the tissue is washed 3 times and allowed to re-equilibrate to basal rate. The test compound is added to the tissue bath at the desired final concentration. Thirty minutes after addition of the compound, a fresh histamine dose response curve is again obtained. Then the response to histamine in the presence of antagonist is compared to the histamine control response. This procedure is repeated, using fresh tissues, for each concentration of antagonist tested. The result is expressed as the apparent dissociation constant ($pA_2$) of the $H_2$ antagonist as determined by standard procedures. Cimetidine is used as the standard for this test.

The results for a series of compounds of the invention are as follows:

| Compound of Example No. | $pA_2$ Value |
| --- | --- |
| Cimetidine | 6.5 |
| 3 | 6.6 |
| 4 | 6.1* |
| 5 | 7.3 |
| 6 | 7.2 |
| 7 | 7.4 |
| 9 | 8.3 |
| 11 | 7.3* |
| 12 | 8.2* |
| 13 | 7.1* |

*These values are the $pK_B$ values for the compounds tested, and the $K_B$ differs from the $A_2$ value only by the fact that the $A_2$ value reflects the results of three experiments, while the $K_B$ value represents the result of only one experiment.

The results show that the compounds of the invention are highly active $H_2$ antagonists, being more active than the standard compound cimetidine.

EXAMPLE 15

The procedure for testing gastric secretion in the rat, a modification of the procedure of Shay et al., Gastroenterology, 26, 906-13 (1954) is carried out as follows:

Male Charles River rats weighing 200-300 grams are deprived of food but not water for 24 hours prior to use. Water is, however, withheld during the experiment. The rats are weighed, anesthetized, and the pylorus ligated according to the method of Shay et al. Treatment or vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or hemolysis are eliminated. An aliquot of each is frozen for later analysis of $Na^+$, $K^+$ and $Cl^-$ concentration. The pH is measured and 1 ml. of gastric juice is titrated with 0.1 N NaOH to a pH of 7.0-7.4. Titratable acid output is calculated in microequivalents and the percent inhibition of acid output is calculated as follows:

$$\% \text{ Inhibition of Acid Output} = \frac{\text{Acid Output (control)} - \text{Acid Output (Drug)}}{\text{Acid Output (control)}} \times 100$$

The test results for some of the compounds of the invention are as follows:

| Compound of Example No. | Dose (mg/kg) | % Inhibition |
|---|---|---|
| 1* | 16 | 50 |
| 2 | 32 | 79 |
| 3 | 4 | 40 |
| 5 | 32 | 68 |
| 8 | 32 | 84 |
| 9 | 32 | 55 |
| 10 | 4 | 41 |
| 12 | 16 | 75 |

*In rats, this compound has the unique property of significantly lowering $H^+$ ion concentration without affecting the volume of secretion.

The results show that compounds of the invention have significant activity in inhibiting gastric acid secretion.

What is claimed is:
1. A compound having the formula:

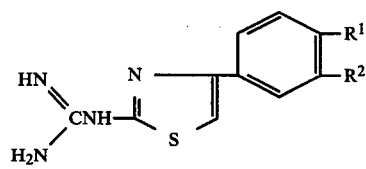

wherein
$R^1$ is hydrogen or cyano(lower)alkyl;
$R^2$ is hydrogen, guanyl, (lower)alkoxyimino, (lower)alkylaminoimino,

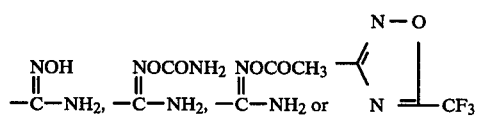

with the proviso that one but never both of $R^1$ and $R^2$ is hydrogen; and the pharmacologically acceptable salts thereof.

2. The compound of claim 1, having the name [4-[4-(cyanomethyl)phenyl]-2-thiazolyl]quanidine.

3. The compound of claim 1, having the name 3-[2-[(aminoiminomethyl)amino]-4-thiazolyl]-N-hydroxybenzenecarboximidamide.

4. The compound of claim 1, having the name N-[(aminocarbonyl)oxy]-3-[2-[(aminoiminomethyl)amino]-4-thiazolyl]benzenecarboximidamide.

5. The compound of claim 1, having the name N-(acetyloxy)-3-[[2-[(aminoiminomethyl)amino]-4-thiazolyl]benzenecarboximidamide.

6. The compound of claim 1, having the name [4-[3-[5-(trifluoromethyl)-1,2,4-oxadiazol-3-yl]phenyl]-2-thiazolyl]guanidine.

7. The compound of claim 1, having the name 3-[2-[aminoiminomethyl)amino]-4-thiazolyl]benzenecarboximidamide.

8. The compound of claim 1, having the name 3-[2-[(aminoiminomethyl)amino]-4-thiazolyl]benzenecarboximidic acid ethyl ester.

9. The compound of claim 1, having the name 3-[2-[(aminoiminomethyl)amino]-4-thiazolyl]-N-methylbenzenecarboximidamide.

* * * * *